US009138521B2

(12) United States Patent
Solomon et al.

(10) Patent No.: US 9,138,521 B2
(45) Date of Patent: *Sep. 22, 2015

(54) DEVICE FOR REMOVING FLUID FROM BLOOD IN A PATIENT

(75) Inventors: Barry A. Solomon, Bedford, MA (US); Gregory S. Erman, Sudbury, MA (US); Frank A. Fazio, Southborough, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 655 days.

This patent is subject to a terminal disclaimer.

(21) Appl. No.: 13/532,506

(22) Filed: Jun. 25, 2012

(65) Prior Publication Data

US 2012/0265118 A1 Oct. 18, 2012

Related U.S. Application Data

(60) Division of application No. 12/380,185, filed on Feb. 23, 2009, now Pat. No. 8,241,239, which is a continuation of application No. PCT/US2007/018636, filed on Aug. 23, 2007.

(60) Provisional application No. 60/839,677, filed on Aug. 24, 2006.

(51) Int. Cl.
*A61M 37/00* (2006.01)
*A61M 1/16* (2006.01)
(Continued)

(52) U.S. Cl.
CPC ........... *A61M 1/1678* (2013.01); *A61M 1/1627* (2014.02); *A61M 1/34* (2013.01);
(Continued)

(58) Field of Classification Search
CPC ... A61M 1/1678; A61M 1/1627; A61M 1/34; B01D 61/145; B01D 63/026; B01D 65/08
USPC .................... 604/4.01–6.16, 27–29, 274–278; 623/11, 12
See application file for complete search history.

(56) References Cited

U.S. PATENT DOCUMENTS 3,579,441 A 5/1971 Brown
4,354,933 A 10/1982 Lester
(Continued)

FOREIGN PATENT DOCUMENTS

EP 0 003 914 A2 9/1979
JP 56051237 5/1981
(Continued)

OTHER PUBLICATIONS

Colton, C.K., "Analysis of Membrane Processes for Blood Purification," *Blood Purification* 5:202-251 (1987).
(Continued)

*Primary Examiner* — Philip R Wiest
(74) *Attorney, Agent, or Firm* — Hamilton, Brook, Smith & Reynolds, P.C.

(57) ABSTRACT

An ultrafiltration device and method for the removal of excess fluid in hypervolemic patients and/or removal of toxins in the blood including for patients suffering from either renal or cardiovascular disease is disclosed. An embodiment of the device includes a housing containing multiple large bore hollow fiber membranes which are connected to the patient's vascular system via a connecting element comprising bifurcated fluid pathway elements to physiologically channel the blood flow either to or from each hollow fiber membrane of the device, a channel to direct the fluid removed by the device to a suitable collection container or the patient's bladder, and controls that control excessive removal of the water from the patient. Devices can be either worn extracorporeally or surgically implanted in order to allow for continuous fluid removal with ambulatory freedom.

23 Claims, 15 Drawing Sheets

(51) Int. Cl.
*A61M 1/34* (2006.01)
*B01D 61/14* (2006.01)
*B01D 63/02* (2006.01)
*B01D 65/08* (2006.01)

(52) U.S. Cl.
CPC .......... *B01D 61/145* (2013.01); *B01D 63/026* (2013.01); *B01D 65/08* (2013.01); *A61M 2209/088* (2013.01); *B01D 2313/10* (2013.01); *B01D 2313/12* (2013.01); *B01D 2313/21* (2013.01)

(56) References Cited

U.S. PATENT DOCUMENTS

| | | | |
|---|---|---|---|
| 5,026,365 | A | 6/1991 | Rossini et al. |
| 5,284,470 | A | 2/1994 | Beltz |
| 5,902,336 | A * | 5/1999 | Mishkin .............. 623/11.11 |
| 5,944,684 | A | 8/1999 | Roberts et al. |
| 6,719,907 | B2 | 4/2004 | Collins et al. |
| 7,332,330 | B2 | 2/2008 | Humes et al. |
| 8,012,118 | B2 | 9/2011 | Solomon et al. |
| 8,241,239 | B2 * | 8/2012 | Solomon et al. ........ 604/6.09 |
| 2002/0052571 | A1 | 5/2002 | Fazio |
| 2003/0114787 | A1 | 6/2003 | Gura |
| 2004/0195165 | A1 | 10/2004 | Bernard et al. |
| 2004/0254514 | A1 * | 12/2004 | Gura ....................... 604/5.01 |
| 2006/0036332 | A1 | 2/2006 | Jennings |
| 2006/0058731 | A1 | 3/2006 | Burnett et al. |
| 2007/0179431 | A1 | 8/2007 | Roberts et al. |
| 2008/0051696 | A1 | 2/2008 | Curtin et al. |

FOREIGN PATENT DOCUMENTS

| | | |
|---|---|---|
| JP | 04-135628 | 5/1992 |
| JP | 2005-508216 | 3/2005 |
| JP | 2006-158626 | 6/2006 |
| WO | WO 84/00885 A1 | 3/1984 |
| WO | WO 95/32736 A1 | 12/1995 |
| WO | WO 97/33474 A1 | 9/1997 |
| WO | WO 98/00172 A2 | 1/1998 |
| WO | WO 98/16171 | 4/1998 |
| WO | WO 98/45028 A1 | 10/1998 |
| WO | WO 03/022334 A2 | 3/2003 |
| WO | WO 2007/103411 A2 | 9/2007 |

OTHER PUBLICATIONS

Gura, V., et al., "Continuous Renal Replacement Therapy for Congestive Heart Failure: The Wearable Continuous Ultrafiltration System," *ASAIO Journal* 52(1):59-61 (2006).

Gura, V., et al., "Continuous Renal Replacement Therapy for End-Stage Renal Disease." In *Cardiovascular Disorders in Hemodialysis*, C. Ronco et al., eds. (Basel:Karger), vol. 149, pp. 325-333 (2005).

Lanza, R.P., et al., "Devices Implanted as AV Shunts." In *Pancreatic Islet Transplantation vol. III: Immunoisolation of Pancreatic Islets*, R.P. Lanza et al., eds. (R.G. Landes) 1994.

Lysaght, M.J., et al., "Filtration Rates and Pressure Driving Force in AV Filtration," *Blood Purification 1*:178-183 (1983).

Maki, T., et al., "Novel Delivery of Pancreatic Islet Cells to Treat Insulin-Dependent Diabetes Mellitus," *Clin. Pharmacokinet.* 28(6):471-482 (1995).

Shaldon, S., et al., "Continuous Ambulatory Hemofiltration," *Trans. Am. Soc. Artif. Intern. Organs XXVI*:210-212 (1980).

Notification of Transmittal of the International Search Report and the Written Opinion of the International Searching Authority, or the Declaration, from PCT/US2009/062967, mailed Jun. 25, 2010, 17 pages.

Notification Concerning Transmittal of International Preliminary Report on Patentability, from PCT/US2008/009891, mailed Mar. 4, 2010, 8 pages.

* cited by examiner

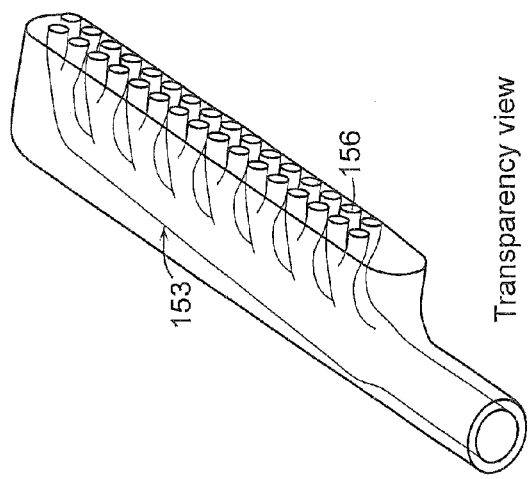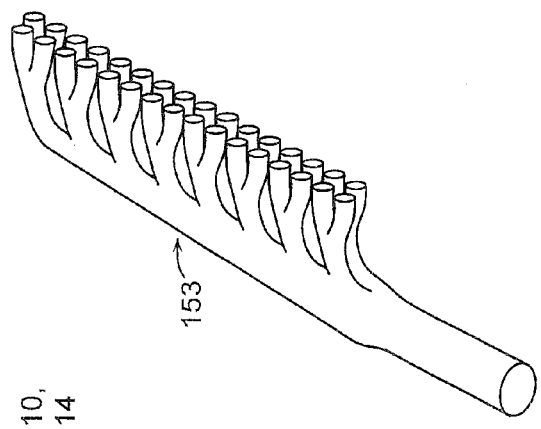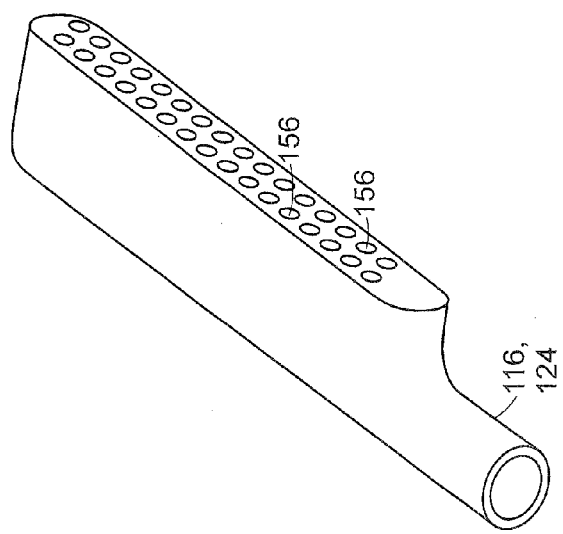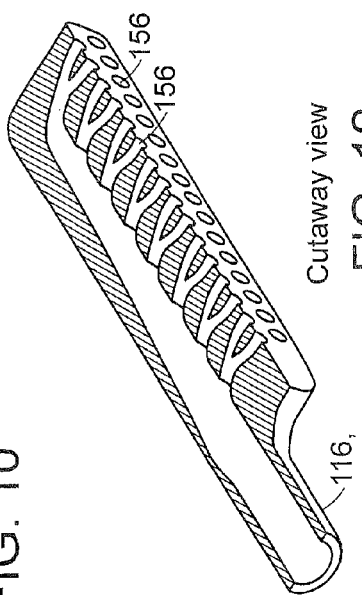

DEVICE FOR REMOVING FLUID FROM BLOOD IN A PATIENT

RELATED APPLICATION

This application is a divisional of U.S. application Ser. No. 12/380,185, filed Feb. 23, 2009 now U.S. Pat. No. 8,241,239, which is a continuation of International Application No. PCT/US2007/018636, which designated the United States and was filed on Aug. 23, 2007, published in English, which claims the benefit of U.S. Provisional Application No. 60/839,677, filed on Aug. 24, 2006. The entire teachings of the above applications are incorporated herein by reference.

FIELD OF THE INVENTION

The present invention relates to filtration devices and methods for continuously treating patients suffering from a condition of fluid overload, retention of excess fluids, or hypervolemia, as may be a result of renal or cardiac disease. The present disclosure also relates to hemodialysis devices for treating people with renal failure. The devices can be worn extracorporeally or surgically implanted into patients.

BACKGROUND OF THE INVENTION

Excessive fluid can accumulate in patients suffering from end stage renal disease (ESRD) or congestive heart failure (CHF). The excess fluid first accumulates in the blood and expands the volume of blood leading to hypertension and places increased stress on the heart. This added stress often leads to heart failure and death. The fluid also can accumulate in the pleural cavities of the lungs leading to shortness of breath. Oxygen uptake in the lungs is reduced as air becomes displaced by water. Again, if this condition is not reversed, death can result.

According to the National Kidney Foundation, 20 million people have Chronic Kidney Disease (CKD) in the US, which is one in every nine Americans. The most severe stage of CKD, when kidneys cease to function, is End Stage Renal Disease (ESRD). According to the USRDS 2005 Annual Data Report, 452,957 people had ESRD in the US in 2003 and, of these, there were 324,826 prevalent dialysis patients. The mortality rate of ESRD patients who receive traditional hemodialysis therapy is 24% per year. The leading causes of death in patients with ESRD are cardiac related which accounts for 43% of all deaths in this population. In ESRD patients, fluid accumulates because their kidneys no longer can effectively remove the water and other fluids, which are consumed daily. The fluid accumulates first in the blood where the blood volume can expand by as much as 20%. The fluid then accumulates throughout the body ending up in the extremities such as the ankles, hands, and other tissues as edema (swelling). Volumes as large as 7-10 liters or about 15-20 pounds can commonly accumulate. This causes increased stress on the heart as evidenced by significant increases in blood pressure or hypertension and subsequent heart failure. About 60% of hemodialysis patients have chronic hypertension as defined by the World Health Organization (WHO) guidelines.

This fluid overload volume can only be removed from ESRD patients by direct ultrafiltration or by the ultrafiltration action of a dialysis procedure, generally carried out weekly in three 4 hour sessions. Removal of the large amounts of water in severe cases of fluid overload often causes fatigue and nausea and, in some cases, arrhythmias, "crashing," and heart failure.

The fluid begins to re-accumulate again once the dialysis session is over. To minimize the fluid accumulation, severe fluid intake guidelines have been established for these patients. Frequently because of continual thirst, however, these fluid restrictions are not complied with because of the hardship they impose on the quality of life of these patients.

After the excess fluid has been removed and the proper blood volume has been obtained, blood pressure will drop and the cardiac stress will be reduced. However, repeated increases and decreases in blood volume may also eventually lead to damage to the heart and vascular system, thus further increasing the risk of cardiac disease. As re-accumulation of water occurs when the patient is not on the machine in a relatively short period of time, hypertension is nearly always present in hemodialysis patients to some degree. For those patients with residual kidney function, this chronic hypertension may cause rapid decay of this residual kidney function leading to the high mortality rates of the general ESRD population rather than the lower mortality rates of those ESRD patients with some residual kidney function.

The incidence of advanced CHF continues to grow and has become a disease of epidemic proportions throughout the world. According to the National Health and Nutrition Examination Surveys, an estimated 4.8 million Americans have CHF. In CHF patients, there is a progressive deterioration of the heart muscle that leads to an inability to pump enough blood to support the vital organs. As a result, fluid retention occurs because the blood perfusion pressure in the kidneys is reduced and the kidneys become inefficient in removing fluid.

While fluid overload in CHF patients can often be treated with numerous pharmacological agents, these drugs become gradually ineffective over time and may also cause undesirable effects such as kidney failure. There continues to be a growing body of literature that supports the concept of physically removing the fluid by blood ultrafiltration, which has been shown to improve patient outcomes and shorten hospital stays and intensive care unit utilization. In fact, fluid removal may be superior to the administration of very large doses of diuretic drugs.

There are several advantages to treating CHF fluid overload patients with ultrafiltration over diuretic drugs. Ultrafiltration offers an efficient fluid removal without those side effects seen with drugs such as kidney failure and blood pressure drops. Furthermore, ultrafiltration quickly relieves the symptoms of shortness of breath and joint swelling.

Ultrafiltration is a process by which blood is exposed (under pressure) to a semipermeable membrane. The membrane properties dictate that water, salts, and other small molecular weight molecules pass through the membrane, but blood cells, proteins, and other large molecular weight molecules are not separated. The ultrafiltration cartridge is generally made up of a very large number of small diameter hollow fiber membranes. Typically, blood is removed from the patient via a catheter placed in an artery or large vein and is pumped into the ultrafiltration cartridge to generate the pressure necessary to carry out the ultrafiltration process. The hollow fibers are arranged so that the blood is perfused through these hollow fiber membranes and the filtered fluid is then removed and discarded, while the treated blood is then returned via another catheter back to the patient.

Conventional ultrafiltration devices have several drawbacks. The procedures are carried out on machines that must be plugged into an electrical circuit and therefore the patients have limited mobility during the typically thrice weekly, 4-hour procedures. Because ultrafiltration is generally carried out during a standard dialysis session, the excessive water volume must be removed in this 4-hour period, which places additional physiological burdens on the patients.

Because of the close relationship between blood volume and blood pressure, there is an additional complication using conventional ultrafiltration procedures related to total amount of fluid removed during a typical session. The fluid amount to be removed is generally determined by the amount of weight the dialysis patient has gained since the last dialysis and/or ultrafiltration session. Excessive fluid removal often leads to a significant drop in the patient's blood pressure (hypotension), which can lead to hemodynamic instability and fainting, cardiac arrest, or death.

There is an increasing body of evidence that continuous removal of accumulated water through daily home dialysis or continuous ambulatory peritoneal dialysis (CAPD) results in significantly improved patient outcomes and far fewer physiological burdens being placed on the patients. However, the complexity and immobility of home dialysis procedures as well as the medical complications, such as infection and scarring, associated with long-term peritoneal dialysis, severely restricts the use of these ultrafiltration procedures to effectively treat hypervolemia.

Another drawback of conventional ultrafiltration is the need to use anticoagulants, such as heparin or citrate, to prevent the blood from clotting in conventional ultrafiltration devices. In order to adapt conventional ultrafiltration devices for continuous use, continuous anticoagulation must be utilized at anticoagulant levels sufficient to prevent clots from forming in the device. Prolonged use of anticoagulants presents a significant risk to patients in general because of the possibility of uncontrolled bleeding occurring and particularly to the majority of ESRD patients who are undergoing thrice weekly hemodialysis procedures during which they also receive anticoagulation.

An additional drawback of the adaptation of conventional ultrafiltration to the continuous treatment of hypervolemia resides in the complications of blood access and the use of pumps. Most blood access for conventional ultrafiltration devices is carried out via indwelling venous catheters or arterio-venous fistulas in the case of certain ESRD patients. Notwithstanding the complications associated with the long term use of these blood access devices, they require the use of special blood pumps in the extracorporeal circuit in order to generate the flow rates and perfusion pressures required to achieve fluid removal in the ultrafiltration device. Blood access catheters that are placed in high pressure arteries have been utilized to obviate the need for additional pumping mechanisms to achieve the blood flow rates and pressures required, but safety concerns for their use outside an intensive care environment render them impracticable.

The use of membrane-based ultrafiltration systems for the treatment of blood has been well documented in extracorporeal systems for over 30 years. However, the use of these systems for continuous applications has been hampered by a number of technical hurdles relating primarily to blood clotting and biocompatibility. Firstly, the cartridges contain a large number of small diameter hollow fiber membranes, which presents a large contact surface for filtration and toxin clearance. While this large surface area, approximately 1-2 $m^2$ (10,000-20,000 $cm^2$) is required to achieve the performance characteristics required for a short term (2-6 hr) extracorporeal ultrafiltration session, it exposes the blood to an equally large surface area of foreign material. The small diameter membranes are used to minimize the extracorporeal volume of blood that is required to be used during typical hemodialysis or ultrafiltration. This combination of large numbers of fibers coupled with their small diameters results in an overwhelming surface-to-volume ratio with which the natural coagulation system of the patient must deal. As a result, a high level of anticoagulation is required to prevent the blood from clotting in the cartridge. While this anticoagulation is medically acceptable over the relatively short period of the hemodialysis or hemofiltration sessions, long-term chronic use of high doses of anticoagulants is medically unacceptable. Even with the use of anticoagulation, continuous use in an extracorporeal circuit of existing dialyzers is generally not possible for more than approximately 48-72 hours.

This inherent thrombogenicity of the existing hollow fiber ultrafiltration devices is further complicated by the design of the inlet and outlet elements of the cartridges which are used in existing devices to (i) distribute blood from a single inlet conduit to the large number of hollow fiber membranes and (ii) to collect the blood from the large number of hollow fiber membranes and channel the blood to a single outlet conduit. These designs allow for a number of stagnation points within these elements of the cartridge increasing the thrombogenicity of existing devices. Furthermore, these elements do not distribute the blood uniformly to all the hollow fiber membranes resulting in significant differences in blood velocity and performance within different areas of hollow fiber membranes.

Secondly, long-term blood access continues to be problematic. Percutaneous catheter use in hemodialysis patients is plagued with issues related to bleeding, infection, and clotting that require a high level of attention to maintain these blood conduits patent for use. There have been some recent developments in catheter design that may improve these catheters, but currently they are unsatisfactory for long-term use due to the persistence of the previously mentioned blood access problems.

The use of large bore, approximately 6 mm diameter, vascular grafts have been largely successful as a long-term blood access conduit in vascular reconstruction surgery. Graft survivals of over 5 years continuous use have been shown with the use of low or no anticoagulants. In a recent study of an implantable membrane device to be used as an artificial pancreas, a 60 cm long coil of 6 mm inner diameter hollow fiber ultrafiltration membrane was implanted into large animals by attaching the device directly to the circulatory system via 6 mm polytetrafluoroethylene (PTFE) vascular grafts as an arterio-venous shunt using the iliac artery and vein. These devices were found to remain patent for periods of up to 4 years without the need for systemic anticoagulation and the patency rate was similar to that found with the 6 mm PTFE graft alone.

The devices and techniques disclosed herein are designed to address these and other deficiencies of prior art devices and techniques for addressing hypervolemia in ESRD and CHF patients through continuous ambulatory volume control and addressing blood toxicity in renal failure patients through hemodialysis.

SUMMARY OF THE INVENTION

The present invention provides methods and apparatuses for continuous blood ultrafiltration and/or hemodialysis which are substantially non-thrombogenic. The disclosure further provides ultrafiltration and hemodialysis apparatuses which can be reliably and safely implanted into the blood circulatory system of patients and continuously and automatically remove excess fluid and/or blood toxins, without the use of perfusion pumps or percutaneous access devices.

Accordingly, one embodiment of the present invention is an apparatus for removing fluid from the body of a patient.

The apparatus includes a first header defining a first flow path with a single inlet and multiple outlets and a second header defining a second flow path having multiple inlets and a single outlet. A filter is in fluid communication with the first header and the second header. A first graft is included for connecting the vascular system of the patient to the single inlet. A second graft is included for connecting the single outlet to the vascular system of the patient. A housing is adapted to collect fluid that passes through the filter. A drain conduit is connected to the housing.

Another aspect of an embodiment of the invention includes the first flow path being adapted to uniformly distribute fluid flow in the first flow path, and the second flow path being adapted to uniformly distribute fluid flow in the second flow path. Uniform fluid flow may be achieved by including one or more flow restricting neck regions or necks in the first flow path, the second flow path, or both. The flow restricting neck regions may be located near one or more of the multiple outlets of the first header, one or more of the multiple inlets of the second header, or both. The flow restricting neck regions near the multiple outlets of the first header may be more flow restrictive the closer they are to the single inlet of the first header. Similarly, the flow restricting neck regions near the multiple inlets of the second header may be more flow restrictive the closer they are to the single outlet of the second header. Uniform fluid flow may also be achieved by having the first flow path progressively bifurcate divergently from the single inlet to the multiple outlets, having the second flow path progressively converging from the multiple inlets to the single outlet, or both.

In a further aspect of an embodiment of the present invention, the first header and the second header are elongated. The first header, the second header, the filter and the housing are substantially coplanar, and their thickness is about 10 mm or less.

In a further aspect of an embodiment of the present invention, the drain conduit may be connected to the bladder of the patient. The patient may then remove the fluid by natural urination. Also, a valve may be adapted to restrict fluid flow through the drain conduit. The valve may be controlled by a sensor and a microprocessor based on physiological parameters of the patient. Alternatively, the valve may be controlled manually.

Another embodiment of the present invention includes a first header having a first inlet and multiple outlets and a second header having multiple inlets. A filter is in fluid communication with the first header and the second header. The first header, the second header and the filter define a flow path. The flow path may include one or more neck regions near one or more of the multiple outlets. The flow path may also include one or more neck regions near one or more of the multiple inlets. The filter may include multiple hollow fiber membranes. The filter may be substantially permeable to water and substantially impermeable to blood cells and proteins.

A further embodiment of the present invention is an implantable hemoconcentrator for removing fluid from the blood of a patient. The implantable hemoconcentrator includes a first header, a second header, and a filter. The filter is in fluid communication with the first header and the second header. The filter includes a plurality of hollow fiber membranes. The first header, the second header and the filter are adapted to define a flow path that provides substantially uniform flow of blood through each of the hollow fiber membranes with minimal stagnation in the flow of blood.

A further embodiment of the present invention is a method for removing fluid from the body of a patient. A fluid removing device is surgically implanted in the patient. The fluid removing device includes a first header defining a first flow path having a first inlet and multiple outlets and one or more necks located near one or more of the multiple outlets. The device also includes a second header with multiple inlets and a second outlet, a filter in fluid communication with the first header and the second header, a first graft for connecting to the vascular system of the patient to the first inlet, a second graft for connecting the second outlet to the vascular system of the patient, a housing adapted to collect fluid that passes through the filter, and a drain conduit to the housing. The first graft is connected to a first blood vessel of the patient, which may be the femoral artery. The second graft is connected to a second blood vessel of the patient, which may be the femoral vein. The drain conduit is connected to the bladder of the patient. The device may be implanted in a subcutaneous location, such as the retropubic space. The method may also include controlling the volume of fluid removed.

Another embodiment of the present invention involves an ultrafiltration device containing a small number of large bore hollow fiber membranes and inlet and outlet distribution elements to evenly distribute and consolidate the fluid flow so as to maximize the efficiency of the device and minimize the disturbance of the blood flow to enable operation of the ultrafiltration device with a minimum of or no anticoagulant.

Another aspect of an embodiment of the present invention is an ultrafiltration device adapted for direct implantation into the patient's blood circulatory system incorporating a material suitable to attach (1) the blood inlet of the ultrafiltration device directly to an artery, (2) the blood outlet of the ultrafiltration device directly to a vein, and (3) the filtered fluid outlet of the ultrafiltration device to the bladder of the patient.

A further aspect of an embodiment of the present invention is an exemplary ultrafiltration device incorporating a system that controls the removal of excess fluid from the circulatory system based upon a change in a relevant physiological parameter, e.g., blood pressure, blood oncotic pressure, blood osmolality, blood constituent level, blood gas levels (e.g., $pO_2$, $pCO_2$) and combinations thereof.

An additional aspect of an embodiment of the present invention is an ultrafiltration device that includes a system to transmit real time diagnostic data.

Devices and procedures according the present invention may eliminate or reduce excess fluid and eliminate or reduce the complications associated with hypervolemia. This will help to reduce the incidence of hypertension and associated cardiac disease. In embodiments of the disclosure the device operates to lower blood pressure and reduce the incidence of pulmonary edema, and allows patients to ingest fluids as needed without the constant concern of controlling and monitoring fluid intake. Such a system is expected to lead to improvements in patient health, quality of life, and patient morbidity and mortality. These improvements may be achieved by slowly and continuously removing excess fluid from patients suffering from hypervolemia.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 9-12 are a series of views of an embodiment of the header and flow paths through the header;

DETAILED DESCRIPTION OF THE INVENTION

A description of example embodiments of the invention follows.

The invention provides methods and apparatuses for continuous blood ultrafiltration and/or hemodialysis which minimize thrombosis in and caused by the apparatuses. The apparatuses so limit apparatus-related thrombosis via the use of variable diameter and/or bifurcating blood channel designs which assure that the blood constituents are not exposed to undue shear forces, while at the same time minimizing the number of blood flow stagnation points. The apparatuses also use large-bore filter fibers that minimize the processed blood's exposure to any thrombogenic filter surfaces within the apparatuses. The present invention provides devices and methods for the ultrafiltration of water, salts and other small molecular weight molecules from the blood. Blood cells and other large molecular weight molecules like proteins are typically not removed from the blood during this ultrafiltration process. The process takes place by exposing blood, contained in one chamber, under pressure to one side of a semipermeable membrane whereby the small molecules contained in the blood are filtered across the membrane, which is then collected in a second chamber. Once treated, the blood is then returned to the body and the filtrate is then discarded. The present invention also relates to devices that can provide hemofiltration and hemodialysis for both volume control and/or toxin removal within the blood.

Figure 1:
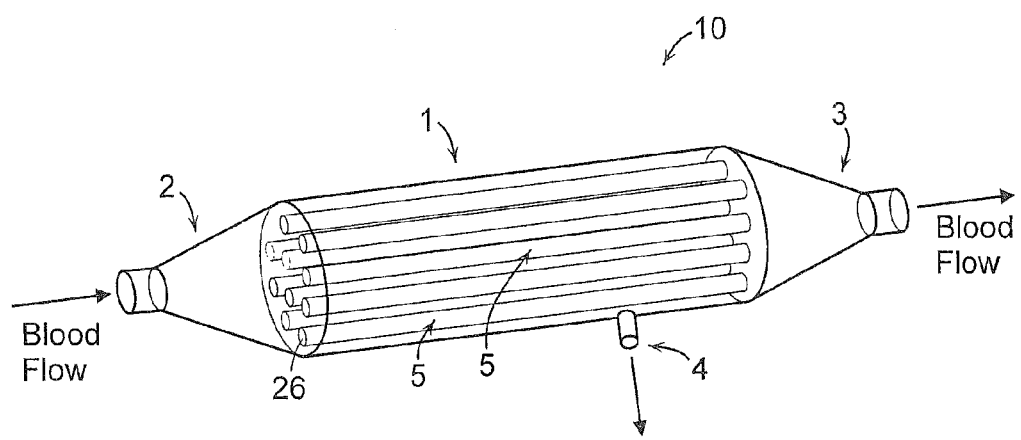
FIG. 1 is a simplified view of a device according to the present disclosure showing a relatively small number of relatively large bore hollow fibers and the inlet and outlet bifurcated distribution elements.

Referring to FIG. 1, an ultrafiltration device 10 is comprised of a bundle of hollow fiber membranes 5 contained within a housing 1. The device contains a conduit 2 to form a single blood flow path into the device and a conduit 3 to form a single blood flow path exiting the device and a conduit 4 for the filtered fluid to exit the device. The conduits 2 and 3 may be referred to as flow headers. The hollow fiber membranes (tubes) 5 can be made of any biocompatible material used for hemodialysis or hemofiltration membranes to remove toxins and/or fluid. These materials include, but are not limited to, polysulfone, cellulose acetate, polyacrylonitrile, or polymethylmethacrylate. The fabrication of these hollow fiber membranes can be accomplished by any number of known methods used in the manufacturing of medical grade hollow fibers for hemodialysis or hemofiltration devices. The housing and conduits of the device can be made of any biocompatible material including, but not limited to, polymers like styrene acrylonitrile (SAN), polycarbonate (PC), polymethylmethacrylate (PMMA), polytetraflouroethane (PTFE), polyethylethylketone (PEEK), polydimethylsiloxane (PDMS), polyurethane (PU), or polysulfone (PS), or metals like stainless steel or titanium, or ceramics. The hollow fiber membranes can be sealed into the housing a variety of biocompatible potting compounds including, for example, polyurethane or epoxy.

An embodiment of an ultrafiltration device according to the present invention preferably produces between 0-4 liters of fluid per day (0-3 ml/min) which is readily achievable in a device containing high flux hollow fiber membranes having a total membrane surface area of less than 600 cm$^2$ when operated at an average transmembrane pressure gradient of about 50 mmHg and a blood velocity of approximately 30 cm/sec. The term high flux refers to the (increased) pore size of the filter element. Dialysers can have increased pore size of the filter element to increase the efficiency of the dialysis treatment. Preferably, the flux is about 1 ml/min/m$^2$/mmhg. In this embodiment, the filter surface area is preferably about 3 to about 6% of the membrane filter surface area of hemodialyzers and hemofilters. Accordingly, devices built according to this embodiment may be considerably smaller than that of existing hemodialyzers and hemofilters. With the reduced size improvement it is possible to design a system that is sized for implantation within the body of hypervolemic patients.

Figure 2:
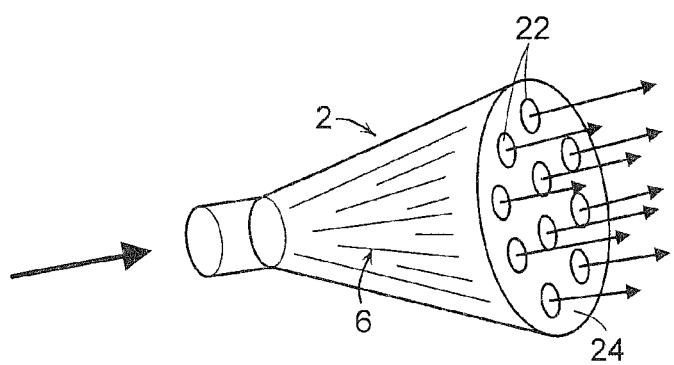
FIG. 2 is a detailed view of a bifurcated distribution element shown in FIG. 1 according to the present invention.
Figure 3:
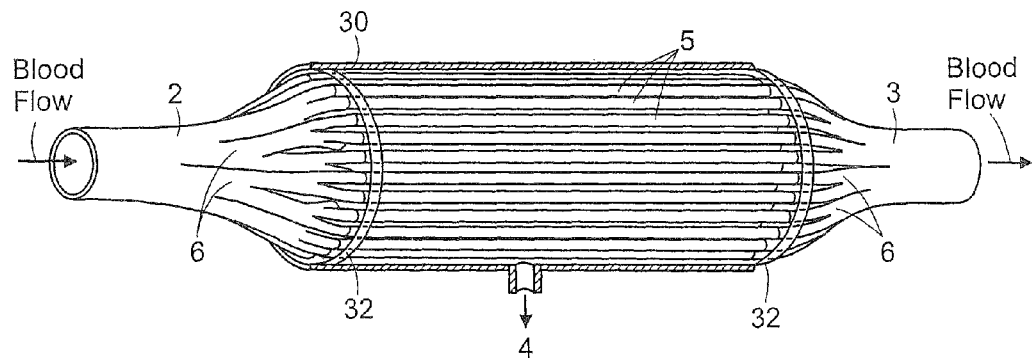
FIG. 3 is a simplified view of the filtration device according to the present disclosure showing the bifurcated distribution elements.
Figure 4:
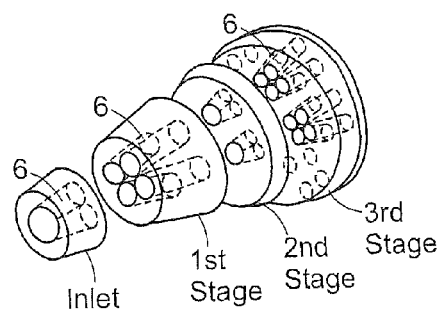
FIG. 4 is an exploded detail view of the bifurcated distribution element according to the present disclosure.

FIG. 2 illustrates the conduit 2 distribution element of the ultrafiltration device according to an embodiment of the present invention that splits and channels the single incoming flow path of blood into discrete flow paths 6 which flow into the core of the hollow fiber membranes. Similarly the conduit 3 (illustrated in FIG. 1) collects and channels the discrete flow paths of blood exiting the hollow fiber membranes into a single exiting flow path. Referring to FIG. 3 and FIG. 4, the design of the flow headers of this embodiment of the disclosure is based on the formation of a bifurcated channel network which optimizes the hydrodynamic forces acting on the blood as it passes through the conduit in a manner so as to minimize the disturbance of the blood flow path and to eliminate any stagnation points within the flow path. In a preferred form, the header diverges into four different conduits at a pass. See for example, FIG. 4. Alternatively, the diverging fluid paths created at a single stage could be more or fewer than 4. Furthermore, significant to the design of this bifurcated network is the angle of divergence for each successive level of fluid splitting. In doing such, the thrombogenicity of the conduit is kept to a minimum, which then minimizes the amount of anticoagulant that is used to maintain the system clot-free throughout its intended use. As illustrated in FIG. 4 the bifurcating header may be constructed in stages where successive stages are aligned to distribute the flow of blood to the filter elements. Bifurcate, as used herein, shall mean to divide or separate into two or more parts or branches.

In a preferred form, the number of hollow fibers contained within the device housing is significantly lower than the number of hollow fibers generally found in many dialyzers. The present invention also provides larger inner diameters of the hollow fiber membranes, in order to prevent clotting in the long-term use of the device. According to one aspect of the present invention, hollow fiber membranes generally used in existing hemodialyzers or hemofilters are smaller than the currently contemplated preferred embodiment. In the device according to the present invention, the number of the hollow fiber membranes is about 12 to about 60 hollow fiber membranes. Further, the hollow fiber membranes have an inner diameter of between about 1 to about 7 mm, about 10 to about 15 times that of most hollow fiber membranes incorporated into hemodialyzers and hemofilters.

The increased inner diameter of the hollow fiber membranes reduces the surface to volume ratio of the membrane and such reduction of surface to volume ratio provides improved thrombogenicity. The lower surface to volume ratio can also lead to a higher device volume per unit surface area than those devices utilizing smaller diameter hollow fiber membranes. However, as noted earlier, the total membrane surface area that appears to be needed to meet the performance requirements of a device according to one embodiment is about (approximately) 3 to about 6% of that in existing hemodialyzers and hemofilters. Specifically, the volume per surface area with hollow fibers (even with inner diameters 10 to 15 times that of most hemodialyzers and hemofilters) is less than 20 ml or about 20% that of common hemodialyzers or hemofilters.

In another aspect of the disclosure, the discrete flow paths emanating from the flow headers 2, 3 are also aligned with the corresponding hollow fiber membranes 5 so as to form a stepless junction between the conduit and the core of the hollow fiber membrane. In a preferred form, conduits 22 are perpendicular to an end face 24 of the header and the fiber membranes are also perpendicular to end face 26 (identified in FIG. 1) of the filter body. A template may be used to precisely align the hollow fibers prior to their being sealed into the housing 1 during the fabrication of the device. Using a template, each hollow fiber membrane is aligned with a discrete blood flow path so that blood flow in all hollow fiber membranes is uniform and turbulent flow or boundary layer separation is significantly reduced or eliminated, maintaining the low thrombogenicity of the overall device. With reference to FIG. 3, the housing 1 may have an external shell 30 that contains the filter elements and endplates 32 that secure the filter element in axial alignment with the device. In a preferred form, the axis of the filter elements are disposed perpendicular to the endplates.

Figure 5:
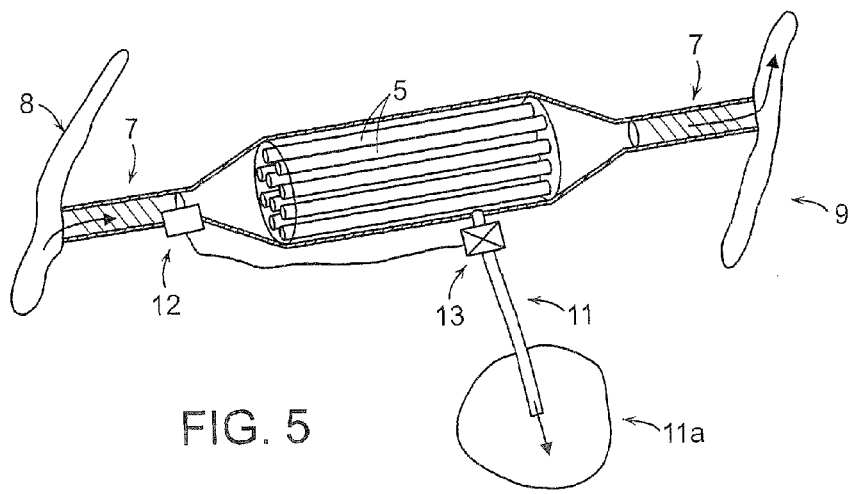
FIG. 5 is a simplified view of the device according to the present disclosure showing implanting a device in a body by attaching the blood path of the device to an artery or vein and attaching the filtrate path of the device to the bladder and showing the device that controls the amount of fluid removed based on a change in a physiological parameter.

Referring to FIG. 5, according to some embodiments, the ultrafiltration device 1 can be modified for implantation directly into the patient by forming a conduit between the inlet of the device and artery 8 using a large bore vascular graft 7 and the outlet of the device and a vein 9 also using a large bore vascular graft 7. By attaching the device as an arteriovenous shunt, the pressure difference between the artery and vein are sufficient to provide the necessary driving force to perfuse the blood through the device and establish a high enough transmembrane pressure to allow the required fluid to be removed from the blood using the small membrane surface area incorporated into the device. The material of the vascular graft can be any material used today for grafts such as polytetraflouroethane (PTFE) or woven Dacron, but the diameter of the graft should be large enough to permit unhindered blood flow to and from the device. In the preferred form, the inner diameter of the vascular graft connections is between 2 mm and 7 mm. The connection between the vascular graft and the device should be such that there is essentially a stepless conduit so as to avoid generating turbulence in the blood flow path and maintain a low level of thrombogenicity in the overall device.

The filtrate from the device in a fully implanted device can readily be collected in the bladder 11a by connecting a suitable conduit 11 between the filtrate outlet of the device and the bladder. The material of this conduit can be of any biocompatible material including, but not limited to, silicone or polyurethane. Many commercially available nephrostomy catheters may be used for this purpose. By using the bladder as the collection site for the filtered fluid, normal urination will periodically remove the fluid from the body and provide for additional capacity for future filtration volumes. Normal urination provides patients with the psychological benefit over use of a urinary bag. However, should the bladder not be functioning in the patient due to chronic atrophy, an external connection via a standard percutaneous catheter can be made between the filtrate outlet of the device and a standard urinary collection bag.

One aspect of the invention provides a system to prevent overfiltration of the hypervolemic patients. In a preferred form, the device is fitted with a control valve 13 on the filtrate outlet of the device. When this valve is closed, no ultrafiltration takes place, but the blood still readily flows through the device maintaining its patency.

In one embodiment, the valve is connected to a blood pressure sensor on the blood inlet conduit of the device so that the inlet blood pressure determines the status of the control valve. At high blood pressures corresponding to the condition of hypervolemia, the filtrate control valve is opened and ultrafiltration of the blood occurs to remove excess fluid. However, as the fluid is removed from the hypervolemic patients, blood pressure will drop correspondingly. When the blood pressure drops to a predetermined level, the sensor sends a signal to the filtrate control valve and the valve is closed and the fluid removal terminates. When the blood pressure increases as excessive fluids subsequently begin to accumulate in the blood, the filtrate valve opens and the ultrafiltration resumes to remove the excess fluid. When the device is used a patient with CHF, the physiological parameter that could be monitored to control the device may be lung capacity or volume. Alternatively, blood parameters such as, e.g., blood pressure, blood oncotic pressure, blood osmolality, blood constituent level, and/or blood gas levels ($pO_2$, $pCO_2$) can be so monitored. Of course, other physiological parameters, even a combination of parameters, could be used to control the device and thus the volume of fluid in the patient.

Figure 6:
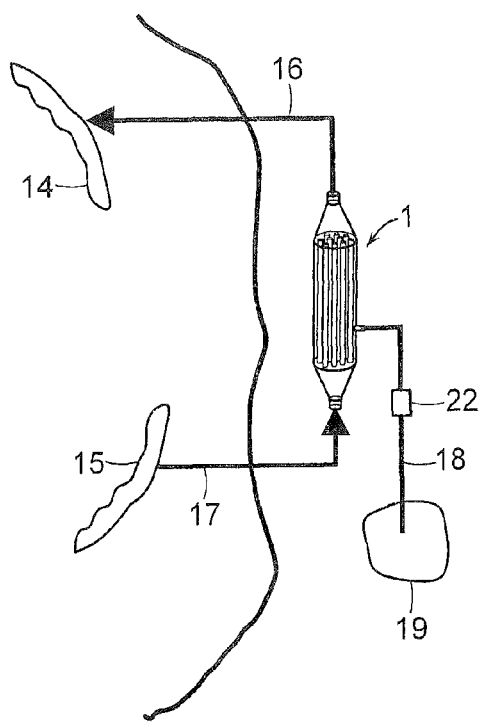
FIG. 6 is a simplified view of the device according to the present disclosure showing a device attached to the vascular system and a collection bag (in the case of a wearable, extracorporeal embodiment)

In another embodiment, the ultrafiltration device is attached external to the body in such a fashion as to permit the patient full range of ambulatory motion. Referring to FIG. 6, the blood inlet of the device 1 is attached to an artery 15 via a percutaneous arterial catheter 17 and the blood outlet of the device is connected to a vein 14 via a percutaneous venous catheter 16. The inherent blood pressure difference between an artery and a vein eliminates the need for an additional blood pump to generate the required blood flow rate and transmembrane pressure difference to establish the ultrafiltration required to alleviate the hypervolemic condition. The filtrate outlet of the device is connected to a standard urinary collection bag 19 via a suitable catheter 18.

In another embodiment, the filtration volume control system is present. The system includes, but is not limited to, a manual on-off valve, an automatic valve connected to a blood pressure sensor, or a battery controlled mini-pump. Methods to immobilize the external elements in one embodiment include, but are not limited to, attaching the external elements to a vest or belt.

Figure 7:
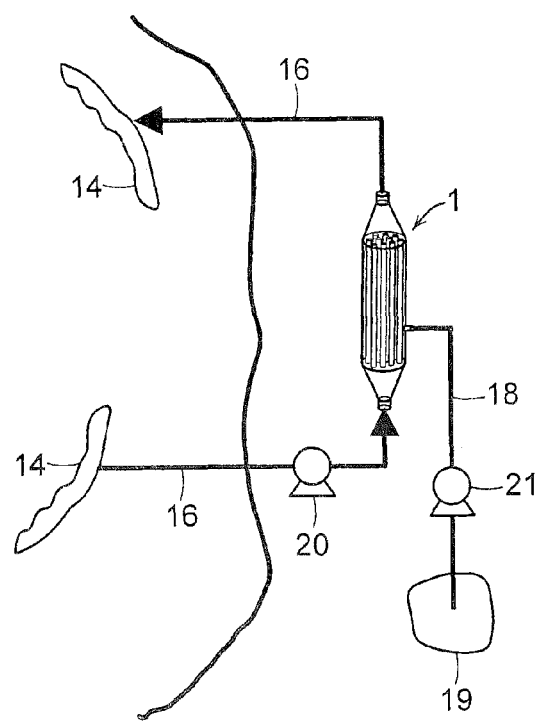
FIG. 7 is a schematic view of a filter device with the connections desirable to implant it in a body.

In another embodiment, referring to FIG. 7, the ultrafiltration device is attached to the blood circulatory system of the patient by attaching both the blood inlet and blood outlet of the device to veins 14 via percutaneous venous catheters 16. However, because there is an insufficient blood pressure gradient between veins, a blood perfusion pump 20 is used to establish the blood flow rate and transmembrane pressure gradient to achieve the required ultrafiltration performance of the device. The transmembrane pressure gradient can also be achieve through the use of a pump 21 on the filtrate outlet conduit to establish a negative pressure in the filtrate chamber, thus creating a sufficient transmembrane pressure gradient to establish the required ultrafiltration performance of the device.

In another embodiment, the device can be used with sensors that have the capacity for real time diagnostic data gathering. For example, blood sensors can be disposed in the conduits, e.g., 7, so that various types of parameters may be measured. Some of the physiological parameters that could be measured include blood cell counts, blood pressure, blood oncotic pressure, blood osmolality, blood constituent level, and blood gas levels ($pO_2$, $pCO_2$) or other parameters that can be productively measured within the bloodstream. The diagnostic data that is collected can be used to operate the device, e.g., open a valve to allow the filter to remove water from the bloodstream. Alternatively, the diagnostic data can be used for some other productive collateral benefit such as regulating medicines or machines to enhance patient comfort.

Figure 8:
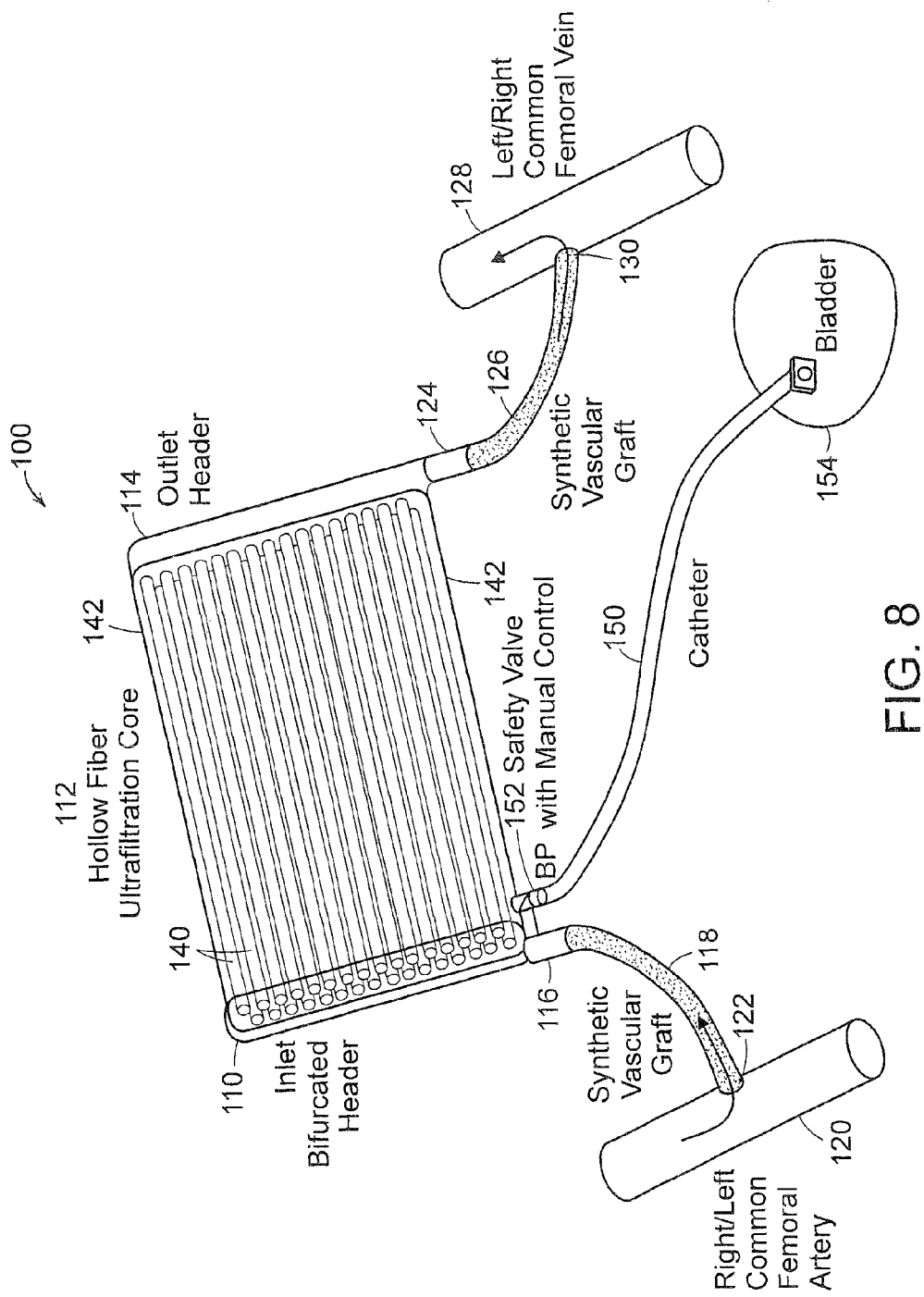
FIG. 8 is a schematic view an embodiment of the filter device that is implantable in a body.

FIG. 8 illustrates a schematic view of an embodiment of an ultrafiltration device 100 that is implantable into the body of a person. The embodiment includes an inlet header 110 and a hollow fiber ultrafiltration core 112 and an outlet header 114. The ultrafiltration core 112 is disposed between the inlet and outlet header in a fluid tight manner. The inlet header 110 includes an inlet conduit 116 that forms an attachment point for a graft material 118 from a femoral artery 120. In a preferred form, the vascular graft is a 6 mm PTFE graft. A cut is made into the femoral artery and the graft material 118 is attached to the femoral artery 120 at location 122 in a known manner. The headers 110 and 114 may alternately be referred to as manifolds or grooved headers.

Similarly the outlet header 114 includes an outlet conduit 124 so that a vascular graft 126 may be attached to the outlet header. In a preferred form, the vascular graft is a 6 mm PTFE graft. The other side of the graft 126 is attached to a femoral vein 128 at an attachment location 130.

Preferably the ultrafiltration device 100 is surgically implanted in a subcutaneous location near and above the groin, such as the retropubic space. This allows for shorter vascular grafts 118 and 126 to connect the ultrafiltration device 100 to the femoral artery 120 and femoral vein 130. In this location the valve 152 can be accessed and adjustments made without penetrating the skin, i.e. extracorporeally (the valve 152 is discussed further below). The surgical procedure can be performed using local anesthesia. The ultrafiltration device 100 can be removed or exchanged in a relatively simple surgical procedure.

The hollow fiber ultrafiltration core 112 includes a multiplicity of hollow fibers 140 that extend from the inlet header 110 and the outlet header 114 in a fluid tight manner. That is, blood that leaves the femoral artery 120 at the attachment point 122 and travels through the graft material 118 and into the header 110 will pass through the header into the plurality of hollow fibers 140. The housing protects the hollow fibers and also collects fluid that passes through the wall of the fibers.

The hollow fibers are connected to the outlet header 114 in a manner similar to the inlet header and fluid that passes through the fibers into the outlet header can be collected in the outlet header and pass through the graft material 126 and back into the bloodstream through the femoral vein.

The housing 142 includes a drain conduit 150 with a valve 152. The valve operates as a safety valve with a manual control so that the device can be properly regulated. The outlet of the drain conduit is configured to drain into the bladder 154. The drain conduit, in a preferred form, may be a Filtrate Suprapubic Malecot Bladder Catheter available through Cook Medical, Bloomington, Ind. The Malecot catheter includes radially expandable distal end to secure the catheter within a bladder. Of course alternative catheters may be used to dispose of the fluid from the device. Additionally, the conduit can be directed outside the body and connected to an ostomy bag. Preferably the device 100 is substantially flat and the components of the device are substantially coplanar as shown in FIG. 8 in order to facilitate implantation of the device in the body of a patient.

The housing 142 and the ultrafiltration core 112 may be constructed out of flexible materials. This flexibility will permit the device 100 to bend or flex, further facilitating the implantation and maintenance of the device in the body of a patient. Alternatively, the housing 142 may be constructed from substantially inflexible material.

FIGS. 9 and 12 illustrate embodiments of the inlet header 110 and outlet header 114. Preferably the inlet header 110 and the outlet header 114 are identical, and they are shown as such in FIGS. 9-12. If the inlet header 110 and the outlet header 114 are identical this will likely streamline design, manufacture and assembly of embodiments disclosed herein.

As shown in FIGS. 9-12, the inlet header 110 defines a flow path 153 beginning at the inlet conduit 116 which then is split or bifurcated into multiple separate flow passages 156. The separate flow passages 156 connect to the hollow fibers 140. Similarly, the outlet header 114 defines a flow path 153 beginning at the separate flow passages 156 at the juncture with the hollow fibers 140 and combines or converges the separate flow passages 156 into a single outlet conduit 124. The flow paths 153 defined by the inlet header 110 and outlet header 114 may be adapted to optimize the hydrodynamic forces acting on the fluid passing through the flow paths 153. FIG. 12 shows a partial cutaway view illustrating the flow path 153.

FIGS. 10 and 11 illustrate the flow paths 153 defined by the headers 110 and 114. As illustrated in FIG. 10-12, the header flow paths 153 are configured to have smoothly diverging/converging conduits. Reference numeral 153 in FIGS. 10 and 11 illustrates the volume of the flow paths 153 themselves. The headers 110 and 114 define the flow path 153. Flow passages 156 are adapted to fit the hollow tubes 140 of the ultrafiltration core 112. As in other embodiments, the connection preferably is made to be as smooth as possible (without discontinuities) so that the possibility of blood clotting is minimized.

The headers 110 and 114 including the corresponding flow paths 153 may be adapted to optimize the hydrodynamic forces acting on the blood as it passes through the flow paths 153 in a manner so as to minimize the disturbance of blood flow and to reduce or eliminate any stagnation points within the blood flow. In a preferred embodiment, there are thirty-two flow passages 156 in each of the headers 110 and 114. In another preferred embodiment there are sixteen flow passages 156 in each of the headers 110 and 114. The angle and path of divergence for each flow passage 156 may be adapted to minimize thrombogenicity in blood flow, which eliminates or minimizes the amount of anticoagulant that must be used to maintain the system clot-free throughout its intended use.

Figure 13:
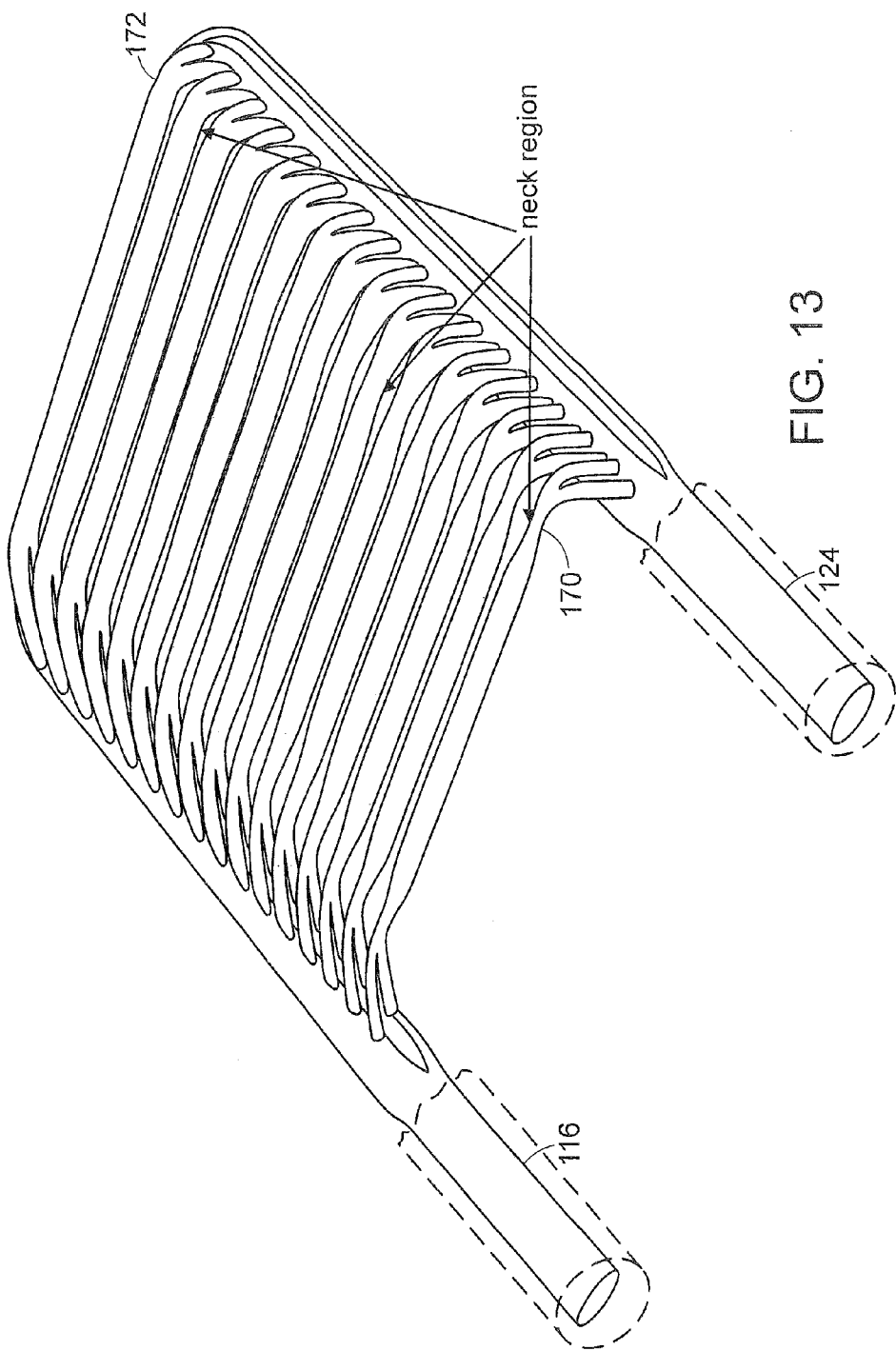
FIGS. 13 and 14 are views of the flow path of the entire device illustrating necking of the flow path.
Figure 14:
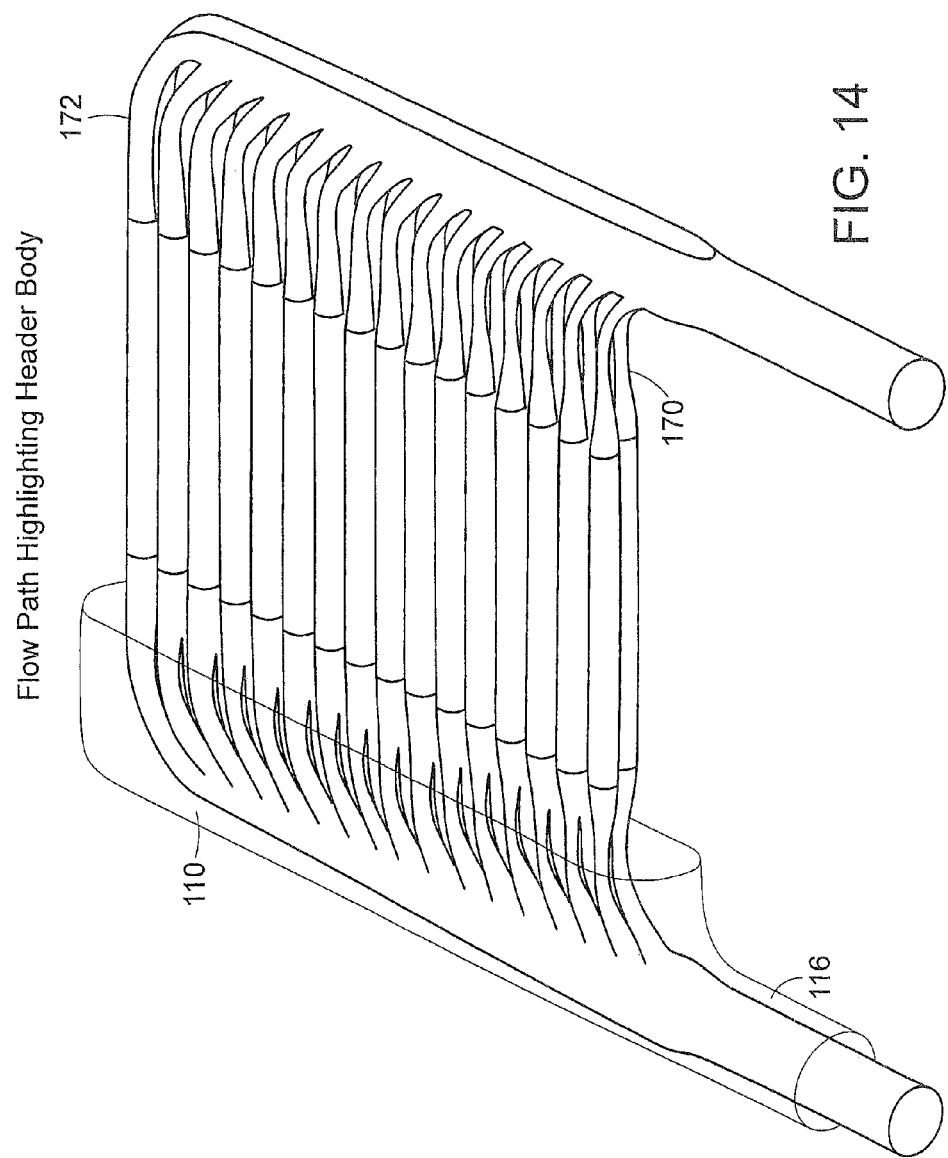

FIGS. 13 and 14 illustrate the flow path through an embodiment of the invention. As shown in FIGS. 13 and 14 the flow path includes neck regions or necks, e.g. 170, 172. Neck regions are shown as constrictions or restrictions in the flow passages 156. Alternatively one or more of the neck regions may be located in the hollow fibers 140, preferably located towards the end of the hollow fibers 140. The neck regions closer to the header inlet conduit 116 and header outlet conduit 124, e.g. 170, are narrower (i.e., more flow restrictive) than the neck regions, e.g. 172, at the regions further away from the header inlet conduit 116 and header outlet conduit 124. The variation in neck region size may be adapted to provide for more uniform volume of blood flowing through each of the hollow fibers 140, minimize blood flow disturbance, and reduce or eliminate any stagnation points within the blood flow.

FIGS. 13 and 14 show an embodiment of the invention with neck regions, e.g. 170, 172, located in the inlet header 110 and the outlet header 114. Alternatively, neck regions could be present only in the inlet header 110 or the outlet header 114. Such an arrangement may require the neck regions to be more constricting as compared to the embodiment with neck regions located in both the inlet header 110 and the outlet header 114.

Figure 15:
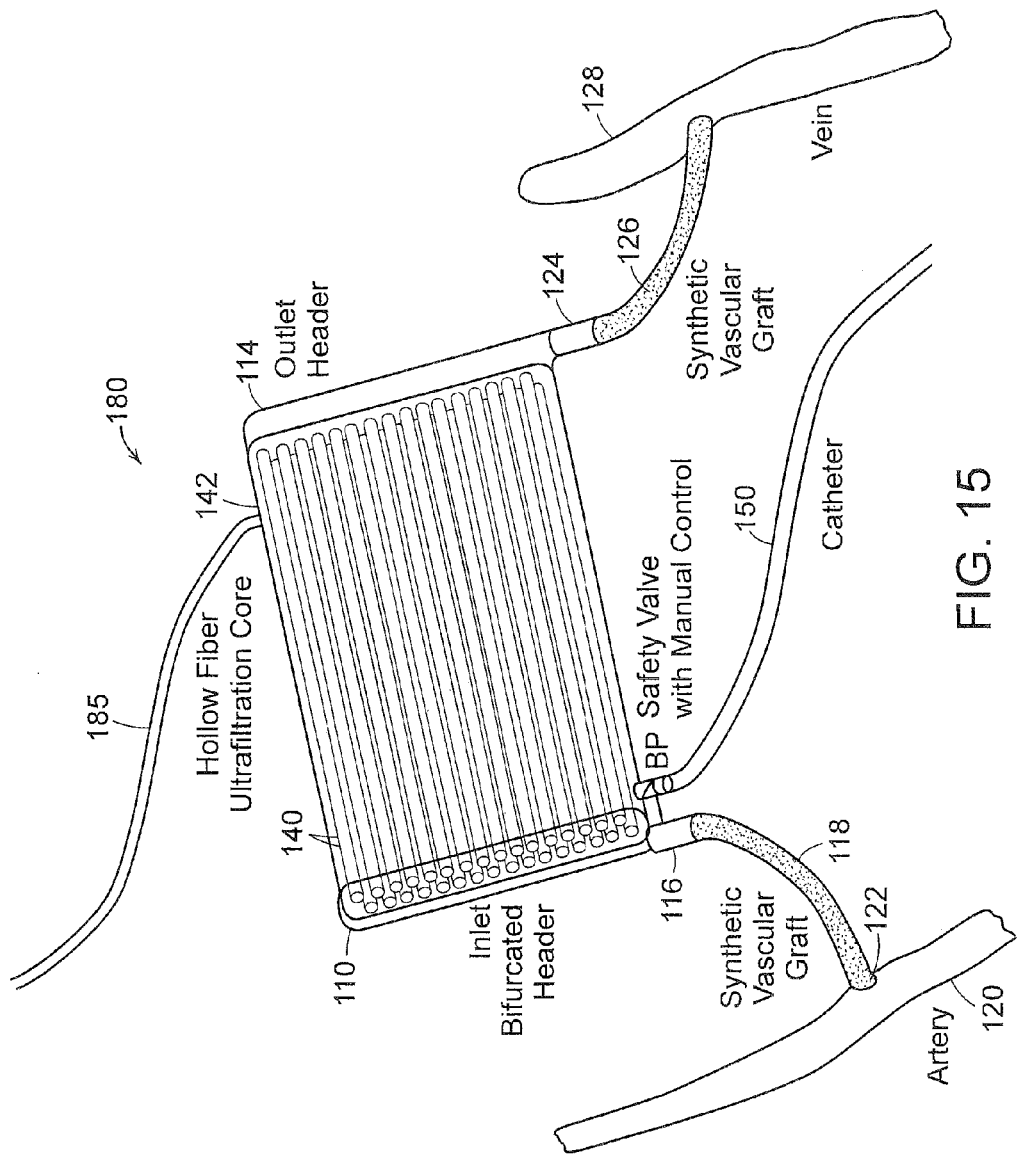
FIG. 15 is a schematic view of a filter device configured to provide hemodialysis.

FIG. 15 illustrates a device configured for hemodialysis. Like reference numerals will be used for like elements from FIG. 8 and need not be described here. In a hemodialysis device 180 a fluid conduit 185 is used to deliver dialysate to the housing 142 so that the filter elements 142 that have blood passing through can remove toxins through a convection gradient across the filter element so that the toxins are removed from the blood into the dialysate and the dialysate fluid is removed from the hemodialysis element.

Figure 16:
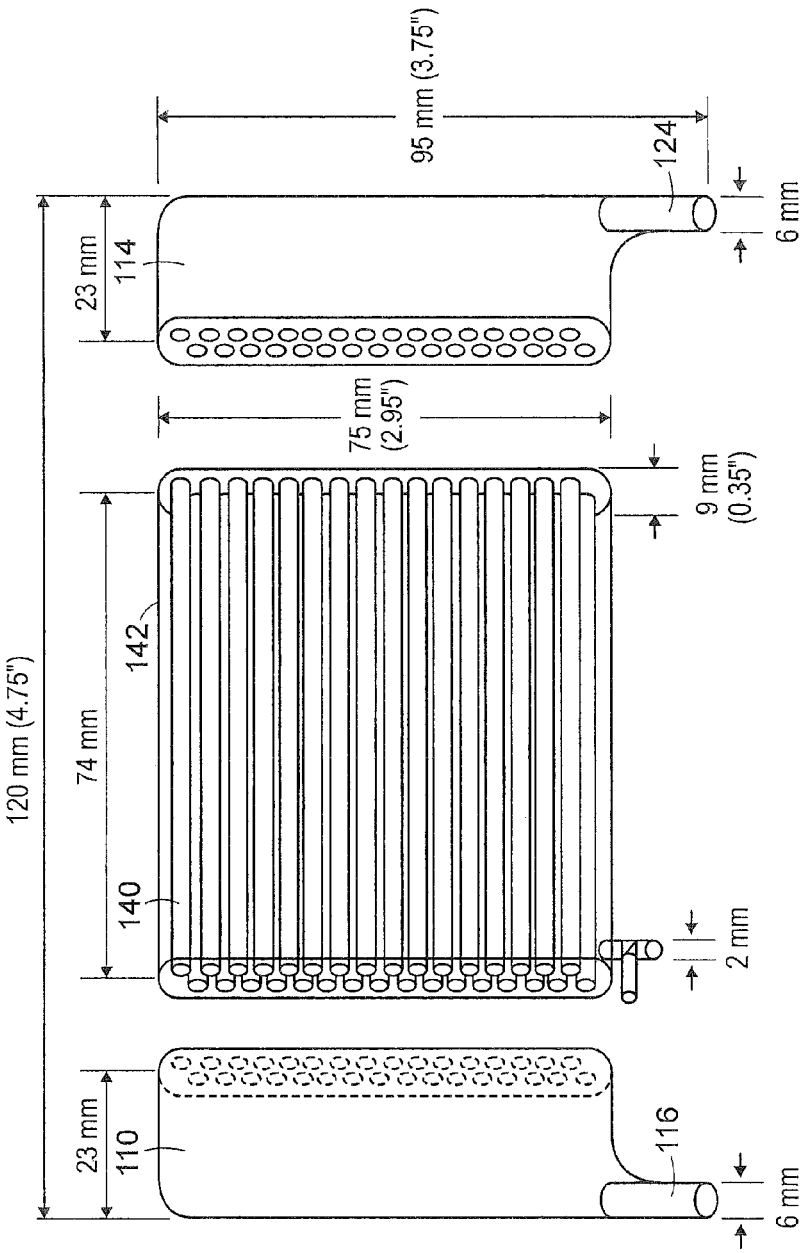
FIG. 16 is a schematic view of a filter device with exemplary dimensions.
Figure 17:
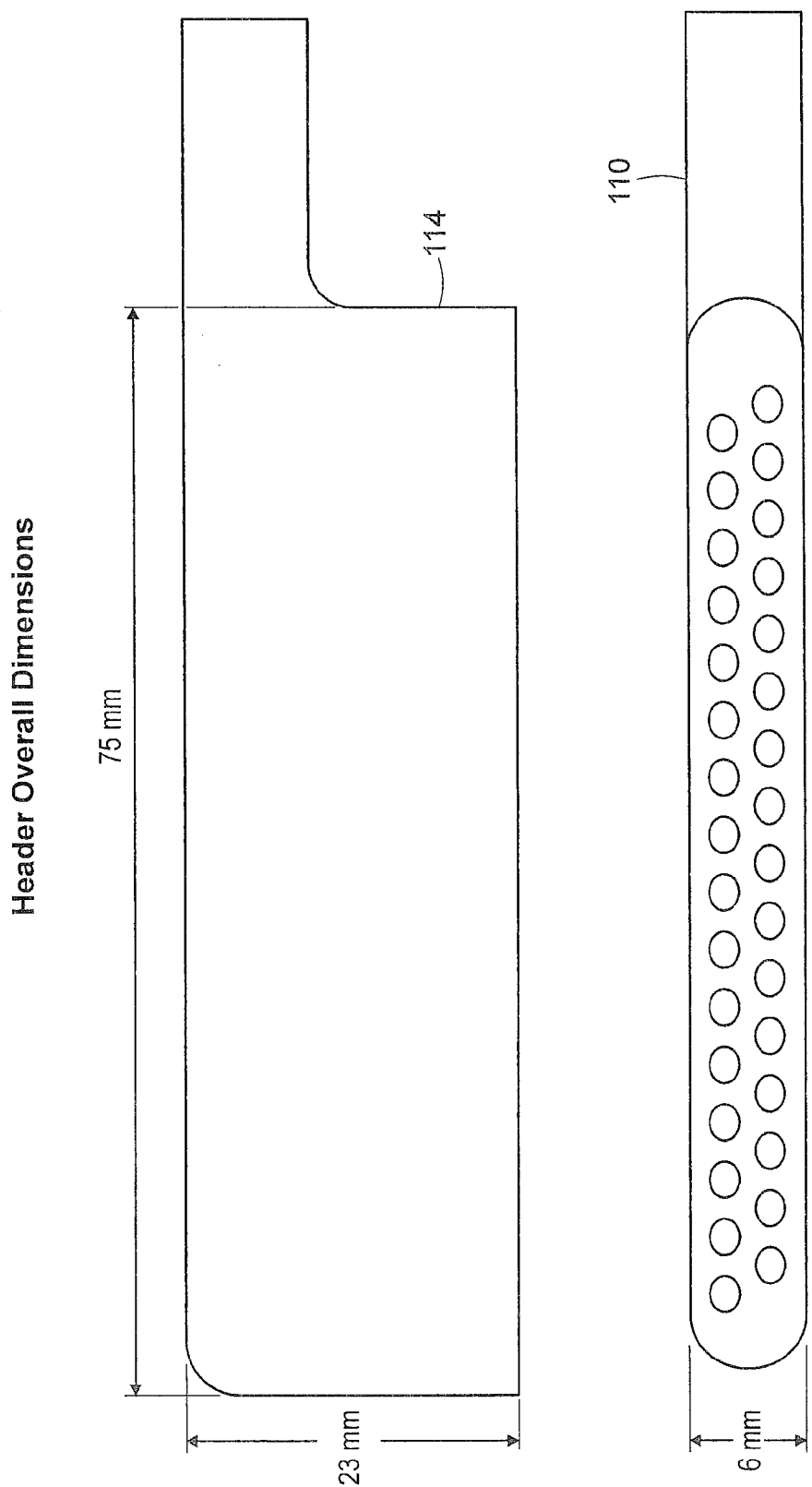
FIG. 17 is a detailed view of the filter header with exemplary dimensions.

FIG. 16 illustrates exemplary dimensions of a device according to the present disclosure. Specifically, as illustrated, the inlet header 110 has an approximately 6 mm inlet and is about (approximately) 75 mm in length. Additionally, the width is approximately 23 mm. The hollow fiber ultrafiltration core 112 is about 74 mm wide and has a length of about 75 mm. About 32 tubes are disposed in the core and are connected to the inlet and outlet. The outlet header 114 has similar dimensions as the inlet header. As illustrated, the headers have an overall length of approximately 95 mm and the inlet/outlet conduit is approximately 6 mm in diameter. FIG. 17 illustrates the header in more detail in two side views taken at 90 degrees apart. As illustrated in the detail header view of FIG. 17, the thickness or dimension across a header 110/114 is about 6 mm. The inlet header 110, outlet header 114, and housing 142 may all be of substantially similar thickness. As shown in FIGS. 16 and 17, the thickness of the inlet header 110, outlet header 114, and housing 142 is about 6 mm. In another exemplary embodiment the thickness may be 8 mm, 10 mm, 12 mm or such other thickness as may be desirable.

Finite element analysis was performed on a device with features substantially similar to those in the embodiments shown in FIGS. 9-12, 16 and 17. FIGS. 13 and 14 are based on the device used in the finite element analysis. The finite element analysis was performed using finite element analysis software from Adina R&D, Inc. and computer aided design drawings produced using software from SolidWorks Corporation. The fluid was assumed to have a viscosity of 0.003 Pa-s. Results of the finite elements analysis are shown in FIGS. 18-20.

Figure 18:
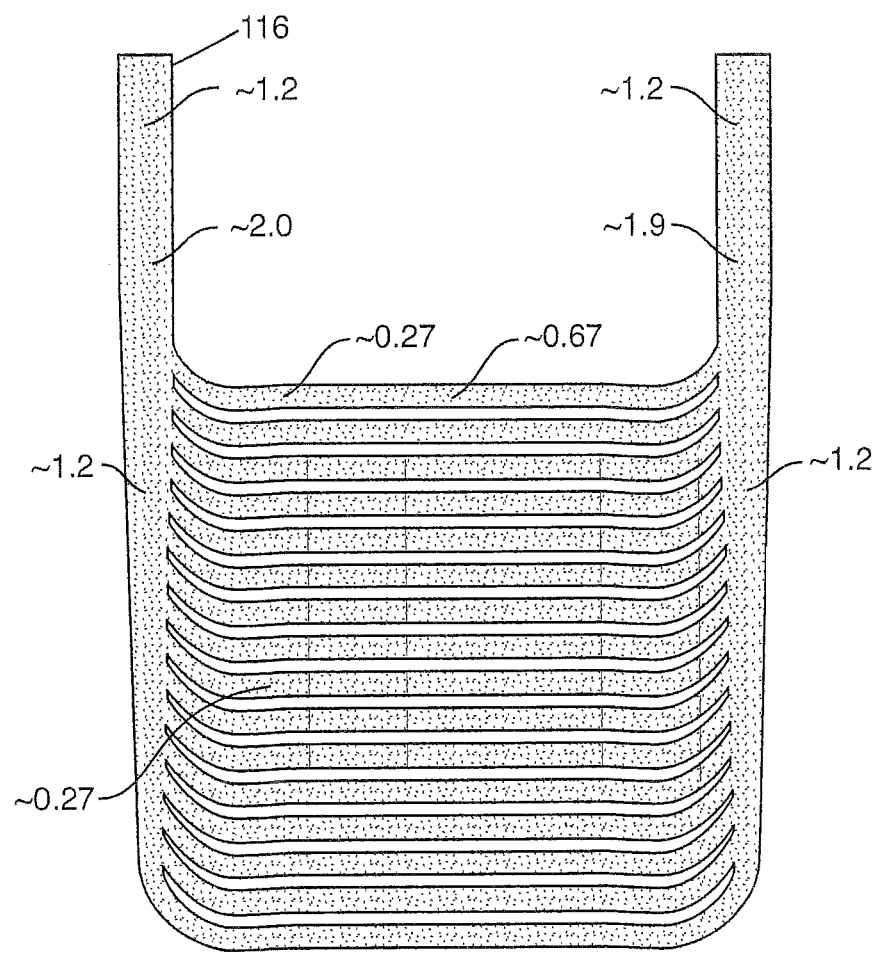
FIGS. 18, 19 and 20 are views of the flow velocity of an embodiment illustrating the effect of neck regions on uniformity of flow.

FIG. 18 shows the velocity of fluid flow through a device that does not include neck regions. The fluid flow through the embodiment exhibits some non-uniform flow through the hollow fibers of the embodiment, especially the hollow fibers closest to the inlet conduit 116 of the inlet header 110 and the outlet conduit 124 of the outlet header 114. Non-uniform flow can result in increased shear forces in the fluid and stagnation points. Approximate fluid flow velocities for this exemplary device are indicated at various points in the device in FIG. 18.

Figure 19:
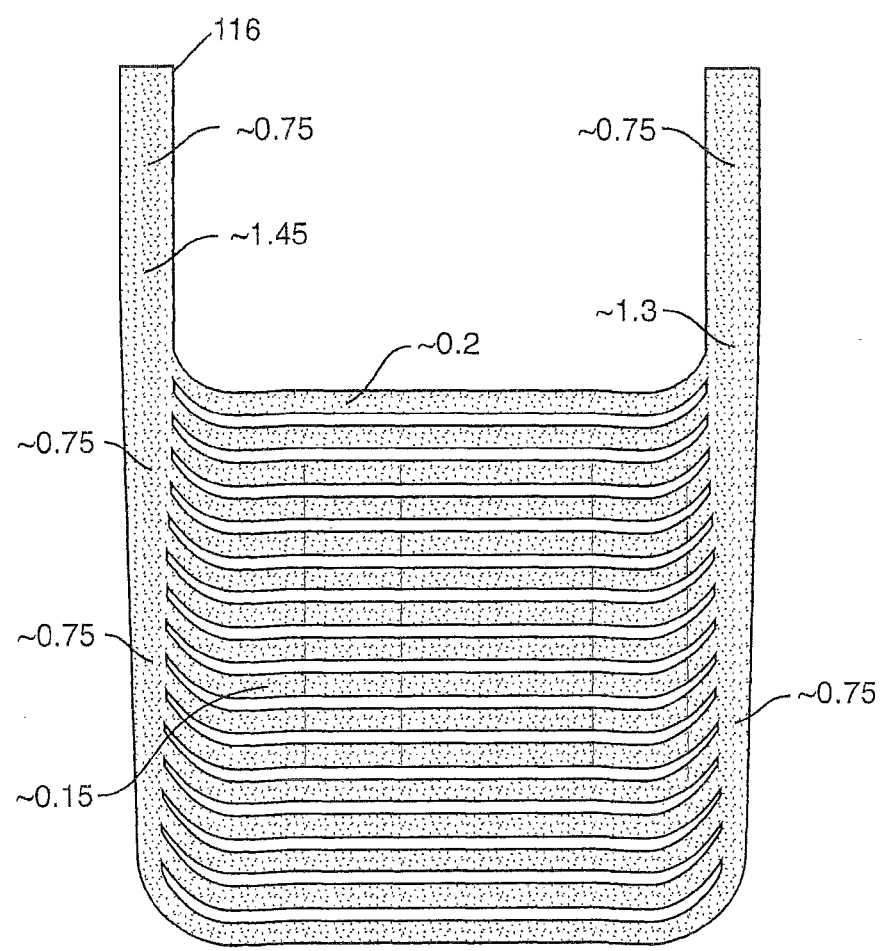

FIG. 19 shows the velocity of fluid flow through a device that includes neck regions. The fluid flow through the device shows significantly reduced non-uniform flow through the hollow fibers of the embodiment as compared to the fluid flow shown in FIG. 18. This is most apparent when comparing the fluid flow through the hollow fibers closest to the inlet conduit 116 of the inlet header 110 and the outlet conduit 124 of the outlet header 114 in FIGS. 18 and 19. Approximate fluid flow velocities are indicated at various points in the device in FIG. 19.

Figure 20:
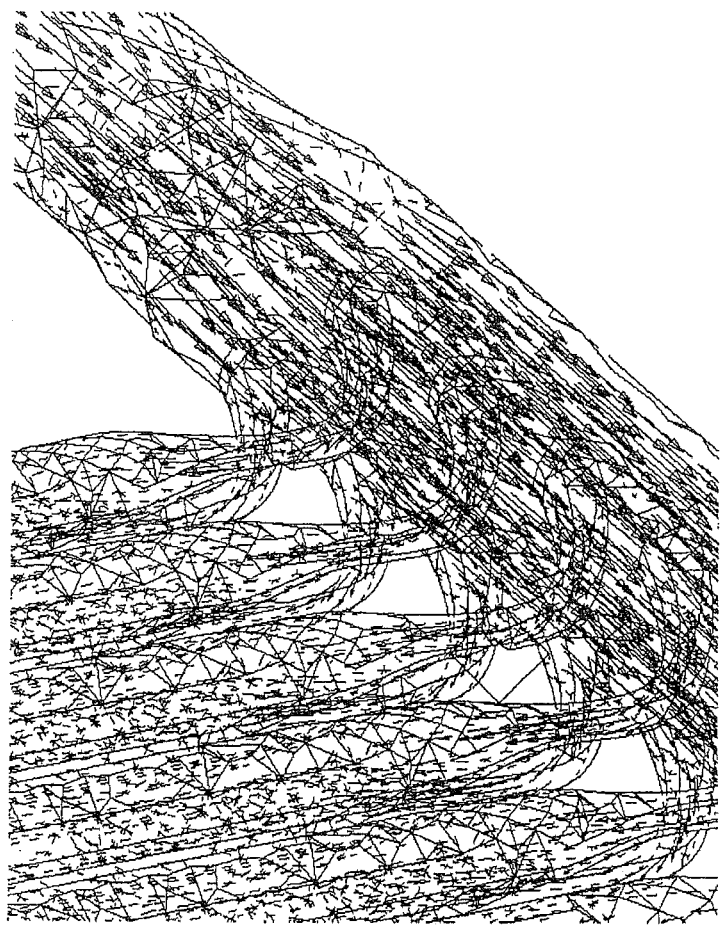

FIG. 20 shows the velocity of the fluid flow through the portion of the embodiment that includes neck regions and is most susceptible to stagnation points and shear forces in fluid. The velocity and direction of fluid flow are depicted using directional arrows. The longer and larger the arrows the faster the fluid is flowing, and conversely the shorter and smaller the arrows the slower the fluid is moving. The arrows in FIG. 20 show uniform fluid flow and no stagnation points in the fluid flow.

Figure 21:
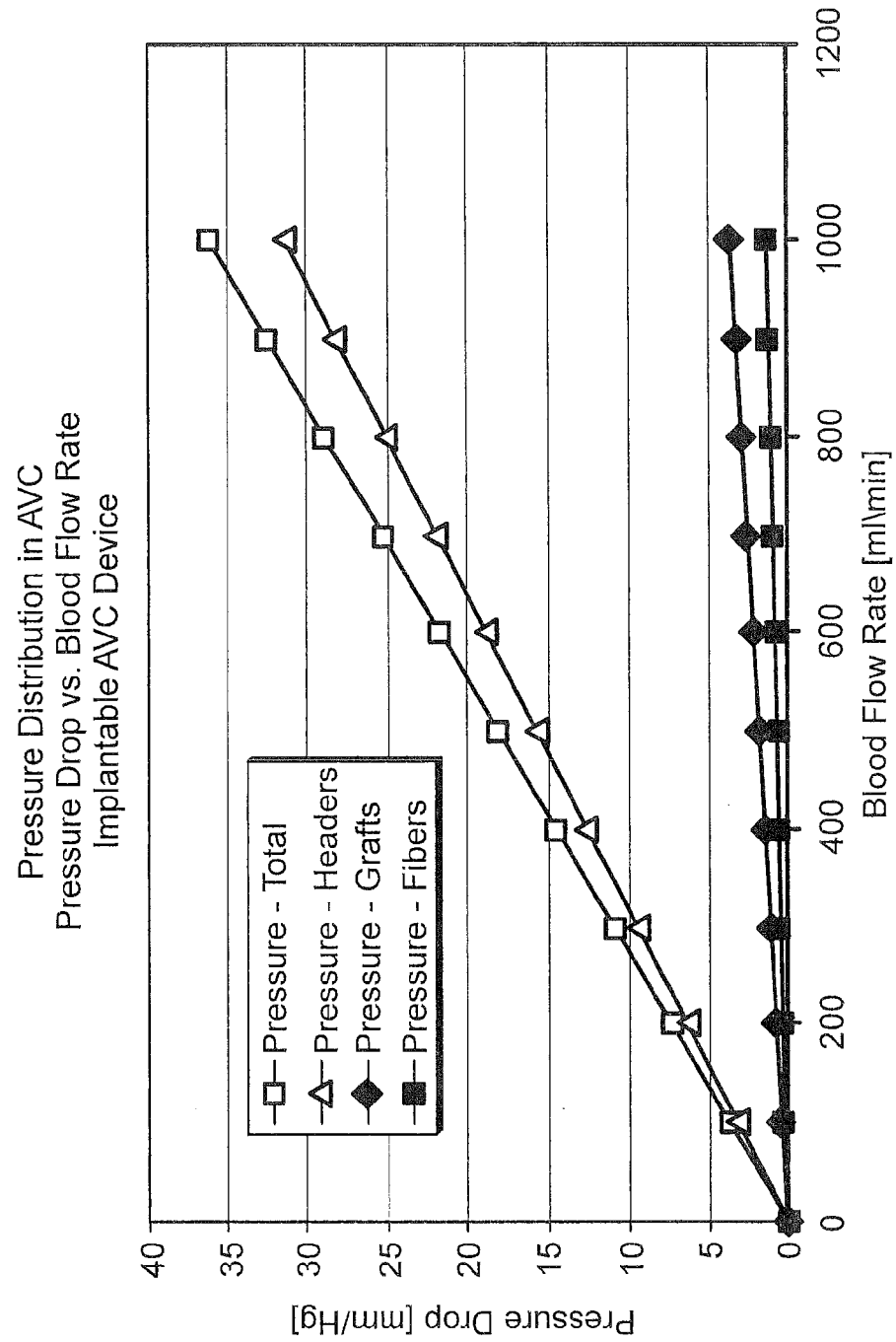
FIG. 21 is a graph showing pressure drop versus blood flow rate through an embodiment of the disclosure.

FIG. 21 is a graph of the results of the finite element analysis described above showing the pressure drop in relation to blood flow rate over the entire embodiment and over portions of the embodiment, such portions including the hollow fibers 140, headers (inlet header 110 and outlet header 114), and the grafts (graft 118 connected to the inlet header 110 and graft 126 connected to the outlet header 114). As is shown in this embodiment, a low pressure drop over the device is achieved.

It is desirable to have a low pressure differential over an ultrafiltration device. The low pressure differential enables the device to be utilized without use of a pump, and therefore makes the device more suitable for implantation. The pressure differential over the embodiment as shown in FIG. 21 is less than the typical pressure differential between a femoral artery and a femoral vein. Typically the femoral artery is approximately 120 mmHg and the femoral vein is at about (approximately) 10-20 mmHg, resulting in a pressure differential of about 100-110 mmHg. Therefore, the typical pressure differential between a femoral artery and a femoral vein is sufficient to cause blood to flow through the device at acceptable rates.

Figure 22:
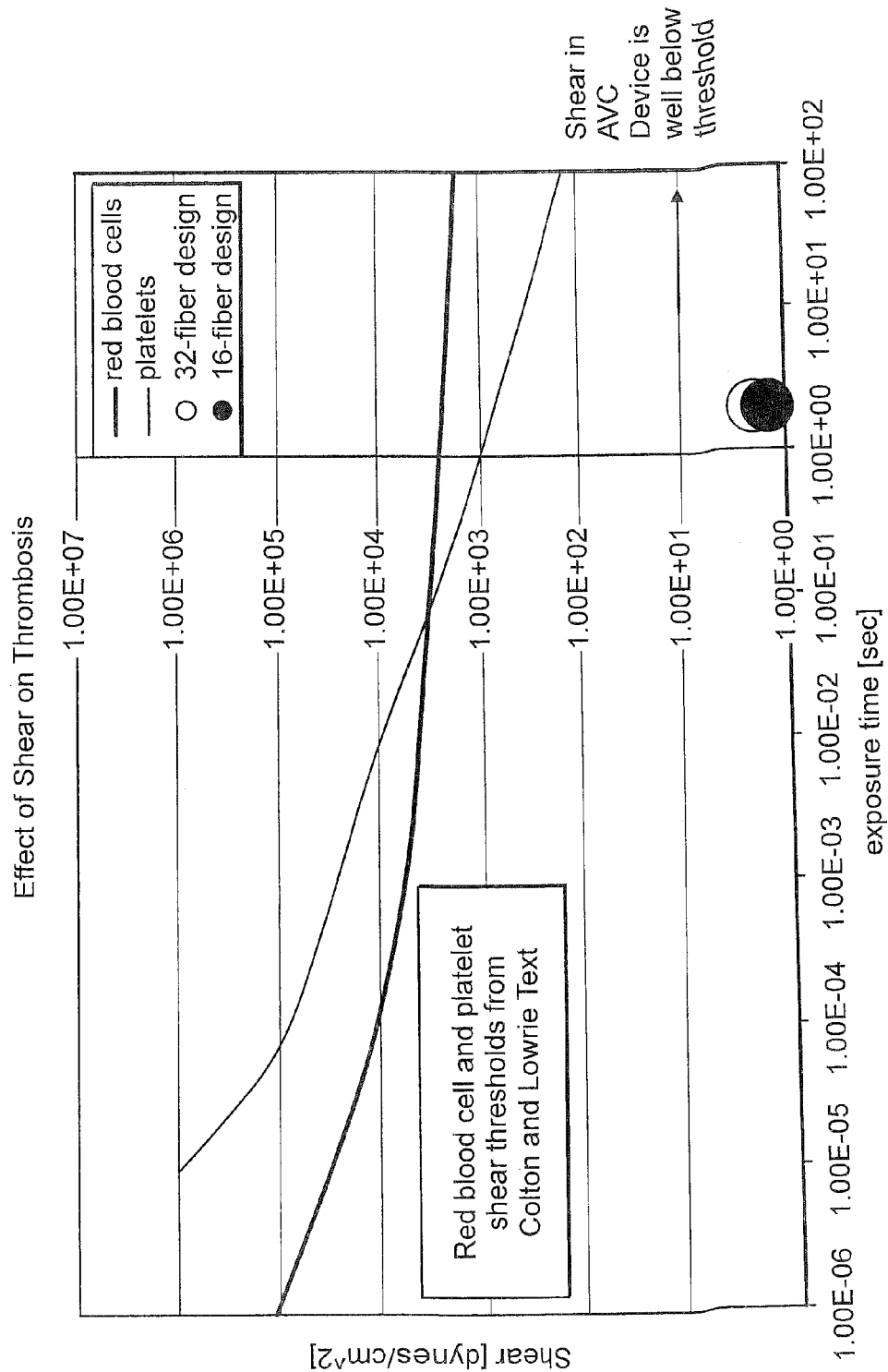
FIG. 22 is a graph showing shear forces versus exposure time for embodiments of the disclosure.

To prevent or reduce the potential of thrombosis occurring in a device it is desirable to minimize shear forces in the blood passing through the device. FIG. 22 is a graph showing shear forces on the y-axis and exposure time on the x-axis. This graph is derived from Colton, C. K. and E. G. Lowrie, "Hemodialysis: Physical Principles and Technical Considerations," in "The Kidney", 2nd ed., B. M. Brenner and F. C. Rector, Jr., eds., Vol. II, W.B. Saunders, Philadelphia, Pa., pages 2425-2489 and in particular page 2441 (1981). The lines on the graph indicate the threshold points above which thrombosis is more likely to occur in red blood cells and platelets. Also included on the graph are the results of finite element analysis as described above. Finite element analysis results for embodiments with sixteen and thirty-two hollow fibers 140 are shown on the graph. The results place these embodiments below the lines on the graph, indicating that thrombosis is not likely to occur in connection with the sixteen and thirty-two hollow fiber 140 embodiments.

To reduce or prevent thrombosis in a device it is desirable to (1) minimize shear forces in the blood passing through the device and (2) avoid stagnation points that may be caused by flow irregularities. The results of the finite element analysis demonstrate that the embodiments including the neck regions reduce or eliminate non-uniform flow and therefore reduce shear forces in the fluid and reduce or eliminate stagnation points in the fluid. The elimination or reduction of non-uniform flow and stagnation points reduces the likelihood of thrombosis and causes the embodiments to be more suitable for long term implantation.

Certain benefits may be achieved by using an implantable device rather than a non-implantable device. After implantation of the device, and after an initial healing period, there is a lower risk of bleeding, clotting and infection than with a non-implanted device. In particular, without any percutaneous access the likelihood of infection is reduced because there is less opportunity for bacteria to gain access to the device or the area in which the device is implanted. In addition, there is a lower likelihood of thrombosis because the blood flow through the device remains uninterrupted and there is no exposure to air. Also, patients receiving the implantable device will be able to have greater fluid intake because of the ability to remove excess fluid from the body. This, combined with the ability to urinate, can substantially increase the quality of life for the patient suffering from kidney disease or heart failure.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An apparatus for removing fluid from a patient, comprising:
   a) a first header defining a first flow path having a first inlet and multiple outlets and a plurality of necks located near one or more of the multiple outlets, wherein necks that are closer to the first inlet are more flow restrictive than necks that are farther away from the first inlet;
   b) a second header having a second outlet;
   c) a filter in fluid communication with said first header and said second header;
   d) a graft for connecting the vascular system of the patient to the first inlet;
   e) a graft for connecting the second outlet to the vascular system of the patient;
   f) a housing adapted to collect fluid that passes through the filter; and
   g) a drain conduit connected to the housing.

2. The apparatus of claim 1, wherein said second header defines a second flow path having multiple inlets and one or more necks located near one or more of the multiple inlets.

3. The apparatus of claim 1, wherein the plurality of necks in the first flow path are adapted to promote the uniform flow of fluid through the apparatus.

4. The apparatus of claim 2, wherein the second flow path has a plurality of necks, wherein necks that are closer to the second outlet are more flow restrictive than necks that are farther away from the second outlet.

5. The apparatus of claim 1, wherein the drain conduit is adapted to be in fluid communication with the bladder of the patient.

6. The apparatus of claim 1, wherein the first flow path progressively bifurcates divergently from the first inlet to the multiple outlets.

7. The apparatus of claim 2, wherein the second flow path progressively converges from the multiple inlets to the second outlet.

8. The apparatus of claim 1, wherein said filter comprises a plurality of hollow fiber membranes.

9. The apparatus of claim 1, wherein said filter has a total membrane surface area of about 600 $cm^2$ or less.

10. The apparatus of claim 8, wherein said hollow fibers are between about 1 and about 7 mm in diameter.

11. The apparatus of claim 8, wherein the number of hollow fiber membranes is between about 12 and about 60 hollow fibers.

12. The apparatus of claim 1, further comprising a means for controlling the amount of fluid removed by the apparatus.

13. The apparatus of claim 12, wherein said means for controlling the amount of fluid removed comprises a valve controlled by a sensor and microprocessor monitoring a physiological parameter of the patient.

14. The apparatus of claim 13, wherein the physiological parameter is selected from the group consisting of blood pressure, weight, and lung capacity, blood pressure, blood oncotic pressure, blood osmolality, blood constituent level, blood gas levels, and combinations thereof.

15. The apparatus of claim 1, further comprising a valve adapted to restrict fluid flow through the drain conduit.

16. The apparatus of claim 15, wherein the valve is a manual valve.

17. The apparatus of claim 1, wherein the filter is substantially permeable to water and substantially impermeable to blood cells and proteins.

18. The apparatus of claim 1, wherein said first header, said second header and the filter are substantially coplanar.

19. The apparatus of claim 7, wherein each of the plurality of hollow fiber membranes are aligned with each of the multiple outlets on a one-to-one basis and each of the plurality of hollow fiber membranes are aligned with each of the multiple inlets on a one-to-one basis.

20. The apparatus of claim 18, wherein said first header, said second header and the housing are each less than about 10 mm in thickness.

21. An apparatus for removing fluid from a patient comprising:
   a) a first header having a first inlet and multiple outlets;
   b) a second header; and
   c) a filter including multiple hollow fiber membranes, wherein the filter is in fluid communication with the first header and the second header, the first header, the second header and the filter defining a flow path, the flow path including a plurality of neck regions near one or more of the multiple outlets, wherein the neck regions are progressively less constricting the greater the distance between the first inlet and the multiple hollow fiber membranes.

22. The apparatus of claim 21, wherein the second header has multiple inlets, and the flow path includes one or more neck regions near one or more of the multiple inlets.

23. The apparatus of claim 21, wherein the first header and the second header are elongated members, and the first header, the second header and the filter are substantially coplanar.

* * * * *